(12) United States Patent
Garcia-Bengochea et al.

(10) Patent No.: US 11,484,300 B2
(45) Date of Patent: Nov. 1, 2022

(54) TUBULAR RETRACTOR SECUREMENT FRAME

(71) Applicant: JGMG BENGOCHEA, LLC, Jacksonville, FL (US)

(72) Inventors: Javier Garcia-Bengochea, Jacksonville, FL (US); John Souza, Sr., Monroe, NC (US)

(73) Assignee: JGMG BENGOCHEA, LLC, Jacksonville, FL (US)

(*) Notice: Subject to any disclaimer, the term of this patent is extended or adjusted under 35 U.S.C. 154(b) by 0 days.

(21) Appl. No.: 17/337,629

(22) Filed: Jun. 3, 2021

(65) Prior Publication Data

US 2022/0313238 A1 Oct. 6, 2022

Related U.S. Application Data

(60) Provisional application No. 63/168,250, filed on Mar. 30, 2021.

(51) Int. Cl.
*A61B 17/02* (2006.01)

(52) U.S. Cl.
CPC ........ *A61B 17/0293* (2013.01); *A61B 17/025* (2013.01); *A61B 17/0218* (2013.01); *A61B 2017/0225* (2013.01); *A61B 2017/0256* (2013.01); *A61B 2217/005* (2013.01); *A61B 2217/007* (2013.01); *A61B 2560/04* (2013.01)

(58) Field of Classification Search
CPC . A61B 17/02; A61B 17/0206; A61B 17/0218; A61B 17/025; A61B 2017/0025; A61B 2017/0256; A61B 2217/005; A61B 2217/007

USPC .................................................. 600/201–246
See application file for complete search history.

(56) References Cited

U.S. PATENT DOCUMENTS

| | | |
|---|---|---|
| 7,198,598 B2 | 4/2007 | Smith et al. |
| D629,898 S | 12/2010 | Bigelow |
| 8,088,066 B2 | 1/2012 | Grey et al. |
| 8,876,709 B2 | 11/2014 | Vayser et al. |
| 9,125,587 B2 | 9/2015 | Hawkins et al. |

(Continued)

FOREIGN PATENT DOCUMENTS

WO 2020092080 A1 5/2020

*Primary Examiner* — Eduardo C Robert
*Assistant Examiner* — Christina Negrellirodriguez
(74) *Attorney, Agent, or Firm* — McNees Wallace & Nurick LLC (57) ABSTRACT

A tubular retractor securement frame is disclosed including a mounting bracket, two flexor arms, and a device emplacement oriented to receive and hold in-place a surgical tool. The mounting bracket includes an elastically deformable plate, rails extending about orthogonal from the elastically deformable plate and about parallel to one another, and receptacles facing one another in the rails which are arranged to receive a retractor arm extending from a tubular retractor at a fixed angle. The flexor arms extend from the mounting bracket adjacent to the rails. The flexor arms are positioned so as not to occlude visualization through the tubular retractor and such that applying pressure to flex the flexor arms toward one another shifts the rails to accept or remove the retractor arm into or from the receptacles, and releasing the pressure reverts the rails so as to inhibit the retractor arm from being inserted or removed.

21 Claims, 12 Drawing Sheets

(56) References Cited

U.S. PATENT DOCUMENTS

| | | |
|---|---|---|
| 9,232,886 B2 | 1/2016 | Sutherland et al. |
| 9,247,866 B2 | 2/2016 | Aferzon |
| D771,805 S | 11/2016 | Brooker |
| 9,737,287 B2 | 8/2017 | Gifford et al. |
| 10,105,042 B2 | 10/2018 | Davis et al. |
| 10,390,811 B2 * | 8/2019 | Oberländer .......... A61B 1/3132 |
| 10,687,699 B2 | 6/2020 | Lalli et al. |
| 10,881,271 B2 | 1/2021 | Aferzon et al. |
| 2019/0293096 A1 | 9/2019 | Ormonde |
| 2021/0052154 A1 | 2/2021 | Gruteser et al. |

* cited by examiner

TUBULAR RETRACTOR SECUREMENT FRAME

RELATED APPLICATIONS

This application claims the benefit of and priority to U.S. Prov. App. No. 63/168,250, entitled "Frame and Securement Methods for Retractor Attachments," filed Mar. 30, 2021, which is hereby incorporated by reference in its entirety.

FIELD OF THE INVENTION

The present application describes various exemplary devices, systems, and methods for facilitating access to a surgical site within the body, particularly the spine. More particularly, the present application describes devices, systems, and methods useful for managing the flow of fluid, including, but not limited to, evacuation of smoke from within a retractor placed adjacent spinal tissue, for example a tubular retractor. Thus, provided is a frame for securing and supporting retractor tube attachments, including, but not limited to, fluidic removal and/or delivery features.

BACKGROUND OF THE INVENTION

Certain instruments, typically referred to as retractors, are utilized in surgery to retract and retain tissue, organs or the like to provide the surgeon with access to or an unobstructed pathway to an organ, bone, tissue, or specific point in the body. Challenges arise for retractors which are utilized with minimally invasive surgical techniques, wherein minimally sized openings are created in the body rather than relatively large incisions. Tubular devices known as cannula retractors, or spreading retractors, having finger-like extensions or blades, are inserted into a small opening and through or around body tissues, muscles, tendons, ligaments, etc., thereby minimizing damage to the body. The surgeon then performs the necessary procedure through the retractor tube using specially designed tools and equipment.

A particular challenge with known retractors used in minimally invasive surgery, particularly tubular retractors, is that such retractors present a small portal to the surgical site, with a circumferential wall that is relatively long and not open to air circulation, such that smoke and aerosolized material stagnate within the tube and occlude visualization. This issue may be addressed by using hand-held instruments; however, this is a less-than-ideal solution limited in utility because using hand-held instruments requires multiple hands in the surgical field around the retractor, and the hand-held instruments and multiple hands themselves occlude visualization. There are examples in the art of devices for attaching fluid movement instruments; however, such known devices are either relatively unstable, or, if stable, such known devices are cumbersome, obstruct the surgical field, and, in some examples, extend the height of the tube in a manner that unacceptably restricts access to the surgical site.

There is a need for securement frames for tubular retractors which are stable and which do not unacceptably restrict access to the surgical site.

BRIEF DESCRIPTION OF THE INVENTION

In an exemplary embodiment, a tubular retractor securement frame is disclosed including a mounting bracket, a first flexor arm, a second flexor arm, and a first device emplacement. The mounting bracket includes an elastically deformable plate, a first rail extending about orthogonal from the elastically deformable plate, a second rail extending about orthogonal from the elastically deformable plate such that the second rail is about parallel to the first rail, and a first pair of receptacles disposed facing one another, one each, in the first rail and the second rail, the first pair of receptacles being arranged to receive a retractor arm extending from a tubular retractor at a first fixed angle. The first flexor arm extends from the mounting bracket adjacent to the first rail and the second flexor arm extends from the mounting bracket adjacent to the second rail. The first device emplacement is oriented to receive and hold in-place a surgical tool disposed at least partially within the tubular retractor at a fixed position and orientation relative to the tubular retractor when the mounting bracket is mounted to the retractor arm. The first flexor arm and the second flexor arm are positioned such that applying pressure to flex the first flexor arm and the second flexor arm toward one another expands a distance between the first rail and the second rail sufficient to accept the retractor arm into the first pair of receptacles and for the retractor arm to be removed from the first pair of receptacles, and upon releasing the pressure the distance between the first rail and the second rail reverts so as to inhibit the retractor arm from being inserted or removed from the first pair of receptacles. The first flexor arm and the second flexor arm are positioned so as not to occlude visualization through the tubular retractor when the mounting bracket is mounted onto the retractor arm.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

The following Reference Numeral Key describes various features as shown in the drawings and relating to the various embodiments as set forth in the description and     1—Tubular Retractor 27—Projection
    2—Tubular Retractor Body 28—Clip
    3—Tubular Retractor Lip 29—Rotatable Channel Member
    4—Inner Wall 30—Leur Adapter
    5—Retractor Arm 31—Crossbar
    6—First Fixed Angle 32—Terminal Face
    7—Tubular Retractor Distal End 33—Flexor Arm Receiver
    8—Tubular Retractor Through Channel 34—Securement Slot
    9—Surgical Tool 35—Mounting Clip
    10—Tubular Retractor Securement Frame 36—Bridge
    11—First Flexor Arm 37—Second Fixed Angle
    12—Second Flexor Arm 38—Additional Surgical Tool
    13—Bottom Surface 39—Axis
    14—Elastically Deformable Plate 40—Securement Arm
    15—Cantilever Snap-Fit Connector 41—Second Device Emplacement
    16—Second Pair of Receptacles 42—Second Rail
    17—First Pair of Receptacles 43—Second Hook
    18—First Rail 44—Fourth Hook
    19—Third Hook 45—Mounting Bracket
    20—First Hook 46—Distance
    21—First Device Emplacement 47—Thickness
    22—Elongate Channel 48—First Cantilever
    23—Receiver Channel Guide 49—Second Cantilever
    24—Channel 50—Actuation Action
    25—Groove 51—Projection
    26—Receptacle 52—Restrictor This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The shortcomings in the art have been overcome by the instant invention which provides a device and system that ensures stable fixation to a tubular retractor that does not obstruct the surgical field and provides a variety of options for affixing one or a combination of fluid movement and light sources that are low profile and occupy only nominal space within the tubular retractor.

Referring to FIGS. 1-7, in one embodiment, a tubular retractor securement frame 10 for mounting on a tubular retractor 1 includes a mounting bracket 45, a first flexor arm 11, a second flexor arm 12, and a first device emplacement 21. The tubular retractor 1 includes a tubular retractor body 2, a tubular retractor lip 3, an inner wall 4, a retractor arm 5 with a first fixed angle 6, a tubular retractor distal end 7, and a tubular retractor through channel 8.

The mounting bracket 45 includes an elastically deformable plate 14, a first rail 18 extending about orthogonal from the elastically deformable plate 14, a second rail 42 extending about orthogonal from the elastically deformable plate 14 such that the second rail 42 is about parallel to the first rail 18, and a first pair of receptables 17 disposed facing one another, one each, in the first rail 18 and the second rail 42. The first pair of receptacles 17 are arranged to receive a retractor arm 5 extending from a tubular retractor 1 at a first fixed angle 6. As used herein, "about orthogonal" indicates being with 15° of orthogonal in each dimension, and "about parallel" indicates being within 15° of parallel.

The first flexor arm 11 extends from the mounting bracket 45 adjacent to the first rail 18. The second flexor arm 12 extends from the mounting bracket 45 adjacent to the second rail 42.

The first device emplacement 21 is oriented to receive and hold in-place a surgical tool 9 disposed at least partially within the tubular retractor 1 at a fixed position and orientation relative to the tubular retractor 1 when the mounting bracket 45 is mounted to the retractor arm 5.

The first flexor arm 11 and the second flexor arm 12 are positioned such that applying pressure to flex the first flexor arm 11 and the second flexor arm 12 toward one another with an actuation action 50 expands a distance 46 between the first rail 18 and the second rail 42 sufficient to accept the retractor arm 5 into the first pair of receptacles 17 and for the retractor arm 5 to be removed from the first pair of receptacles 17. Upon releasing the pressure, the distance 46 between the first rail 18 and the second rail 42 reverts so as to inhibit the retractor arm 5 from being inserted or removed from the first pair of receptacles 17.

The first flexor arm 11 and the second flexor arm 12 are positioned so as not to occlude visualization through the tubular retractor 1 when the mounting bracket 45 is mounted onto the retractor arm 5.

The mounting bracket 45 may further include a second pair of receptacles 16 disposed facing one another, one each, in the first rail 18 and the second rail 42, wherein the second pair of receptacles 16 is arranged to receive the retractor arm 5 extending from the tubular retractor 1 at a second fixed angle 37 distinct from the first fixed angle 6. The inclusion of the first pair of receptacles 17 and the second pair of receptacles 16 may accommodate attachment of the mounting bracket 45 to two different tubular retractors 10 wherein each of the two different tubular retractors 10 have retractor arms 12 disposed at different angles relative to the tubular retractors 10. In one embodiment, the second fixed angle 37 is between 1080 and 112°, alternatively between 1090 and 111°, alternatively 110°, and the first fixed angle 6 is between 1180 and 122°, alternatively between 1190 and 121°, alternatively 120°. The mounting bracket 45 may further include any number of additional pairs of receptacles to accommodate tubular retractors 10 having retractor arms 12 disposed at different fixed angles from the tubular retractors 10.

The tubular retractor securement frame 10 may further include a second device emplacement 41 oriented to receive and hold in-place an additional surgical tool 20 disposed at least partially within the tubular retractor 1 at an additional fixed position and orientation relative to the tubular retractor 1 when the mounting bracket 45 is mounted to the retractor arm 5. The tubular retractor securement frame 10 may also include further additional device emplacements to accommodate further additional surgical tools.

The surgical tool 9 (or the additional surgical tool 20) may be any suitable tool, including, but not limited to, a fluid transport assembly providing at least one of suction or irrigation into the tubular retractor 1, a lighting element providing illumination into the tubular retractor 1, or combinations thereof. The first device emplacement 21 (or the second device emplacement 41, or both) may include a leur adapter 30 in fluid communication with the surgical tool 10 (or the additional surgical tool 20) and a remote suction or irrigation source.

The first rail 18 and the second rail 42 may extend from the elastically deformable plate 14 away from the tubular retractor 1 when the mounting bracket 45 is mounted on the retractor arm 5 (as shown) or toward the tubular retractor 1 when the mounting bracket 45 is mounted on the retractor arm 5 (not shown). Whether the first rail 18 and the second rail 42 extend from the elastically deformable plate 14 away from or toward the tubular retractor 1 when the mounting bracket 45 is mounted on the retractor arm 5 determines the relative direction from which the mounting bracket 45 is mounted on the retractor arm 5.

Each of the first flexor arm 11 or the second flexor arm 12 may, independently, include a groove 25 or a plurality of grooves 25 disposed there along, wherein the groove 25 or the plurality of grooves 25 disposed about parallel to an axis 39 of the tubular retractor 1 and facing the tubular retractor 1.

Referring to FIGS. 8-12, in one embodiment, the tubular retractor securement frame 10, further includes a crossbar 31 slidably mounted on at least one of the first flexor arm 11 or the second flexor arm 12. The crossbar 31 reversibly attaches to the mounting bracket 45 so as to secure the surgical tool 9 against an inner wall 4 of the tubular retractor 1. The crossbar 31 may be secured to the mounting bracket 45 with a mounting clip 35. The mounting clip 35 may include a securement slot 34 for reversible locking the mounting clip 35 and crossbar 31 in place. The crossbar 31 includes at least one flexor arm receiver 33 through which one of the flexor arms 11 and 12 pass when the crossbar 31 is slidably mounted thereupon, the at least one flexor arm receiver 33 being disposed between a terminal face 32 of the crossbar 31 and a bridge 36 of the crossbar 31.

Referring to FIGS. 1-7, the first device emplacement 21 may include an elongate channel 22 extending through a receiver channel guide 23 for greater than a thickness 47 of either the first flexor arm 11 or the second flexor arm 12 over which the first device emplacement 21 extends.

Figure 1:
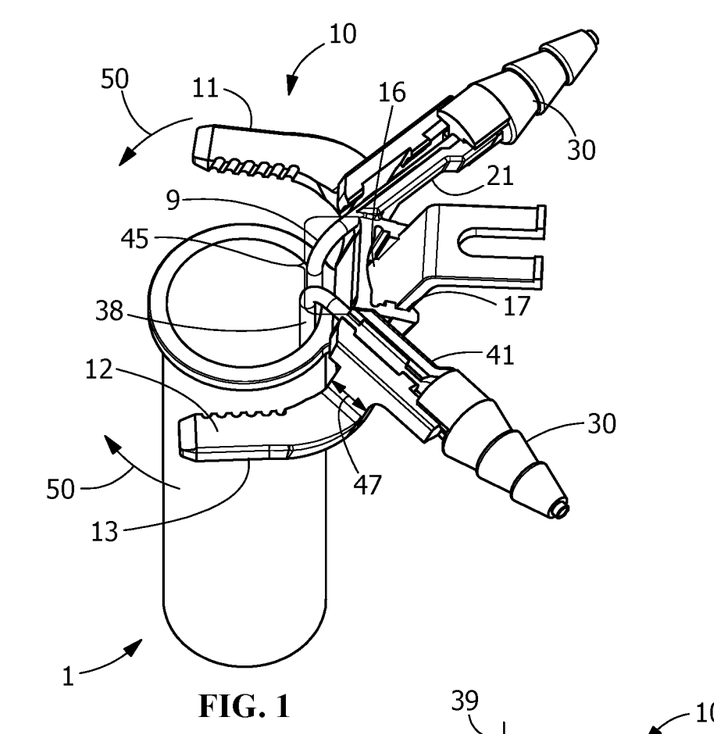
FIG. 1 is a side perspective view of a first exemplary tubular retractor securement frame attached to a tubular retractor and surgical devices, according to an embodiment of the present disclosure.
Figure 2:
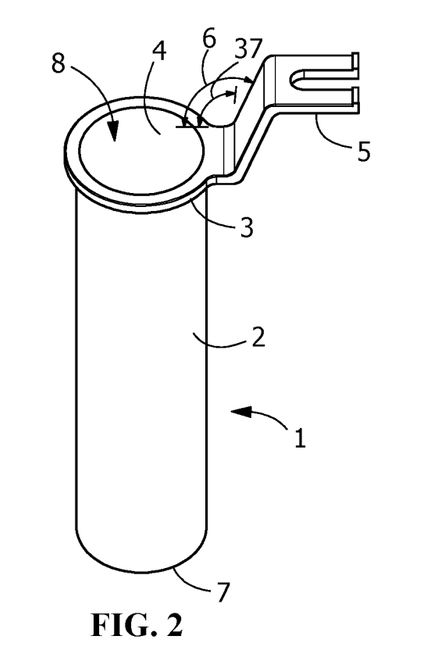
FIG. 2 is a side perspective view of the tubular retractor of FIG. 1.
Figure 3:
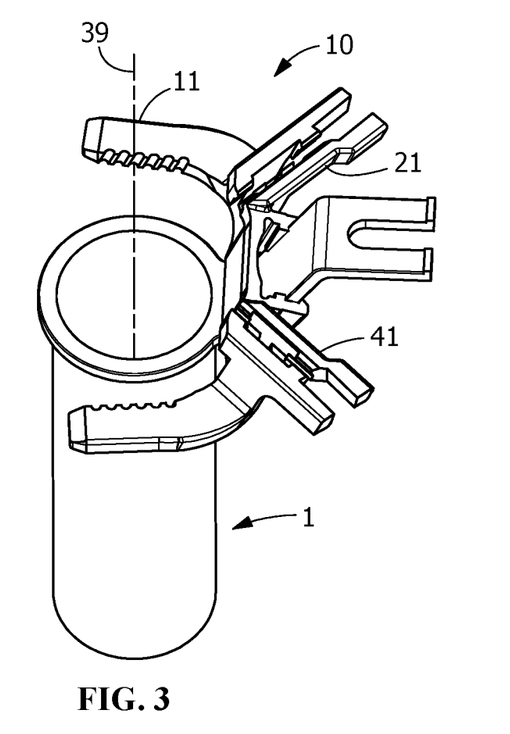
FIG. 3 is a side perspective view of the tubular retractor securement frame attached to the tubular retractor of FIG. 1, according to an embodiment of the present disclosure.
Figure 4:
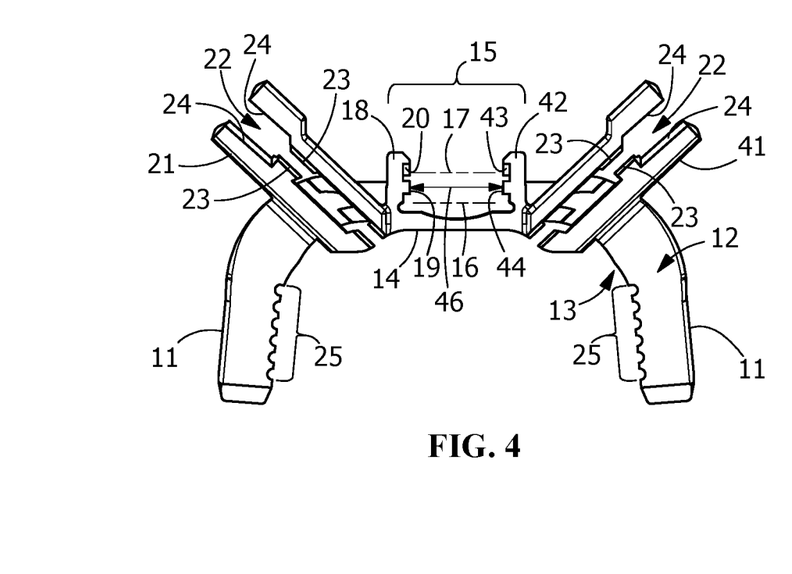
FIG. 4 is a top view of the tubular retractor securement frame of FIG. 1, according to an embodiment of the present disclosure.
Figure 5:
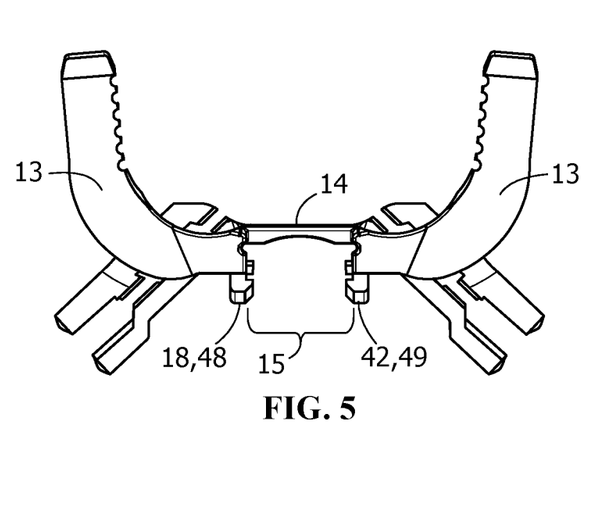
FIG. 5 is a bottom view of the tubular retractor securement frame of FIG. 1, according to an embodiment of the present disclosure.
Figure 6:
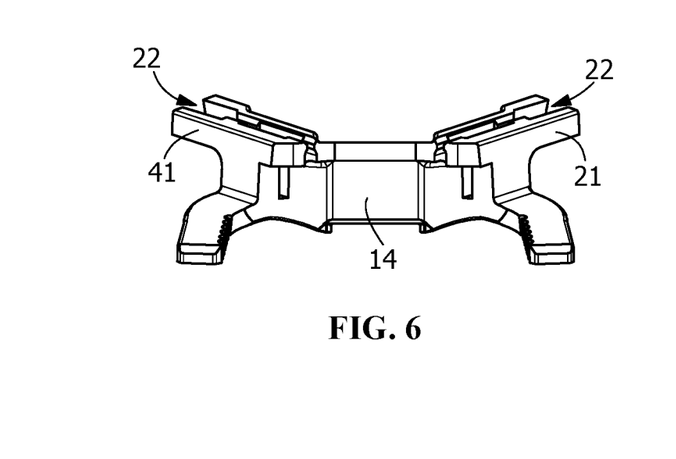
FIG. 6 is a front view of the tubular retractor securement frame of FIG. 1, according to an embodiment of the present disclosure.
Figure 7:
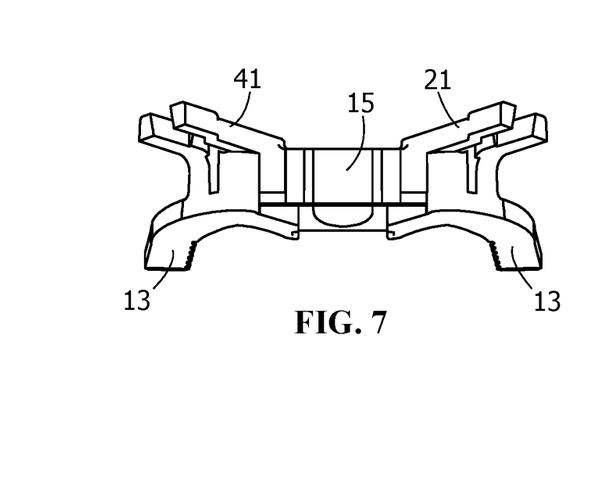
FIG. 7 is a rear view of the tubular retractor securement frame of FIG. 1, according to an embodiment of the present disclosure.
Figure 8:
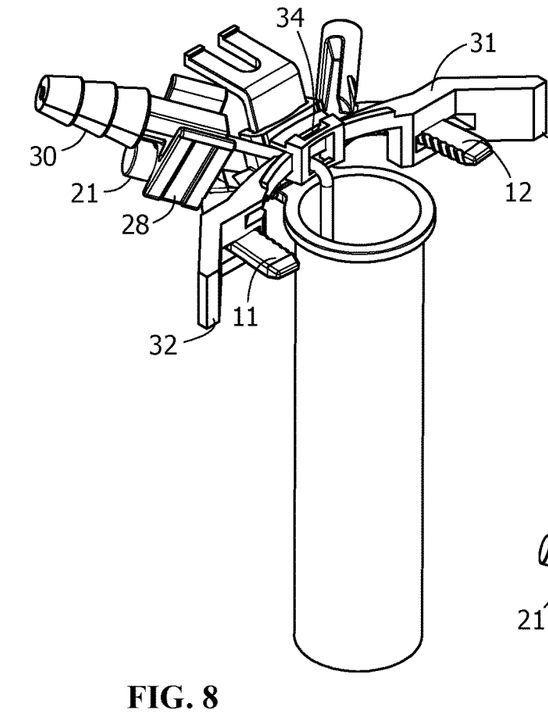
FIG. 8 is a front-side perspective view of a second exemplary tubular retractor securement frame attached to a tubular retractor and a surgical device, according to an embodiment of the present disclosure.
Figure 9:
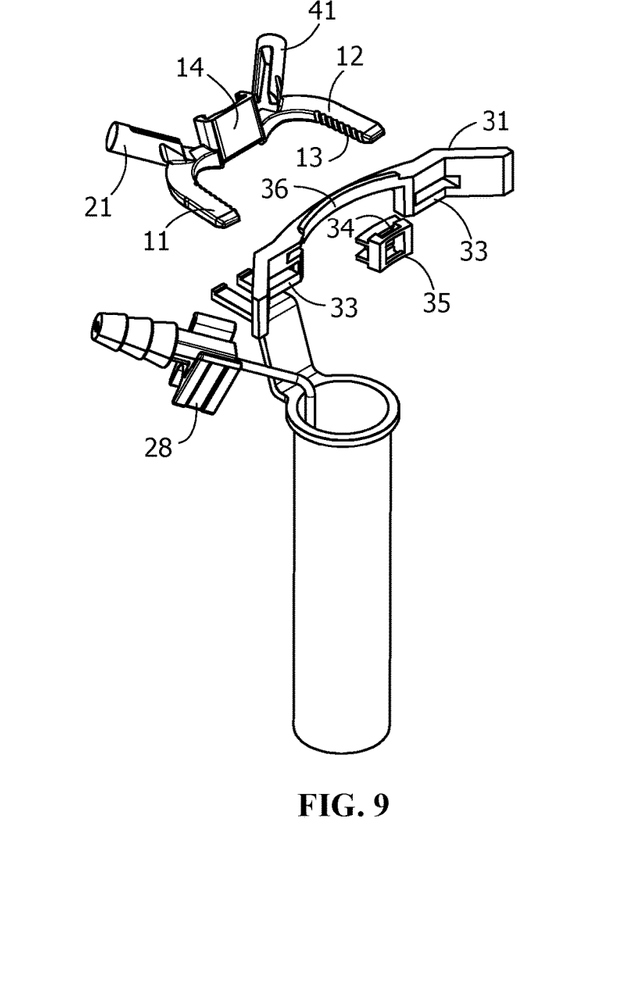
FIG. 9 is an exploded front-side perspective view of the tubular retractor securement frame, tubular retractor, and surgical device of FIG. 8, according to an embodiment of the present disclosure.
Figure 10:
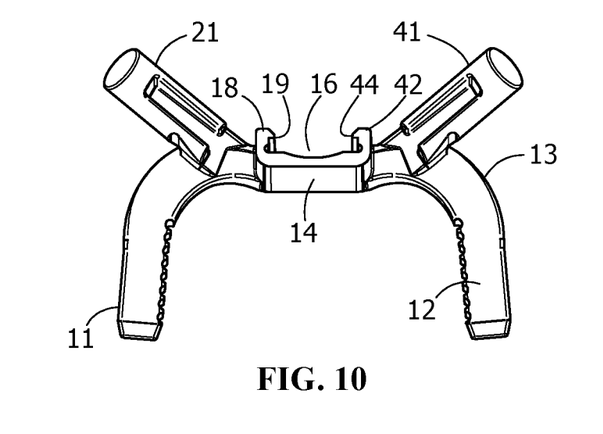
FIG. 10 is a top view of the tubular retractor securement frame of FIG. 8, according to an embodiment of the present disclosure.
Figure 11:
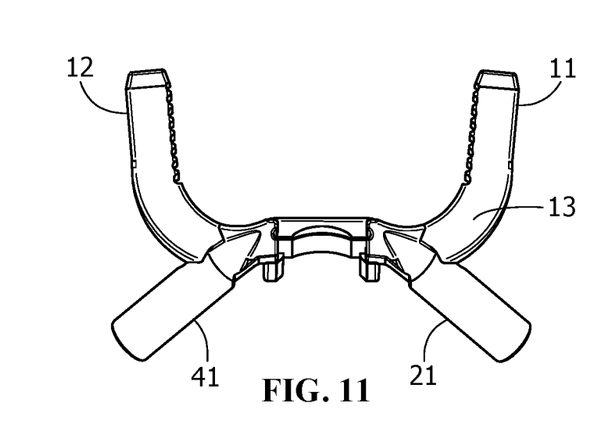
FIG. 11 is a bottom view of the tubular retractor securement frame of FIG. 8, according to an embodiment of the present disclosure.
Figure 12:
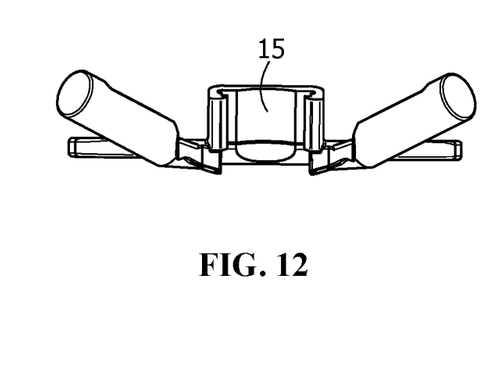
FIG. 12 is a rear view of the tubular retractor securement frame of FIG. 8, according to an embodiment of the present disclosure.
Figure 13:
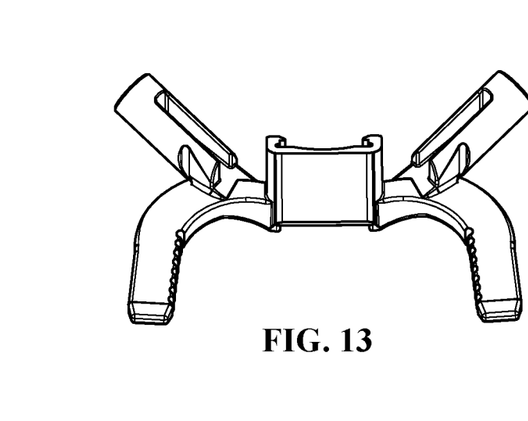
FIG. 13 is a front view of the tubular retractor securement frame of FIG. 8, according to an embodiment of the present disclosure.
Figures 14, 15:
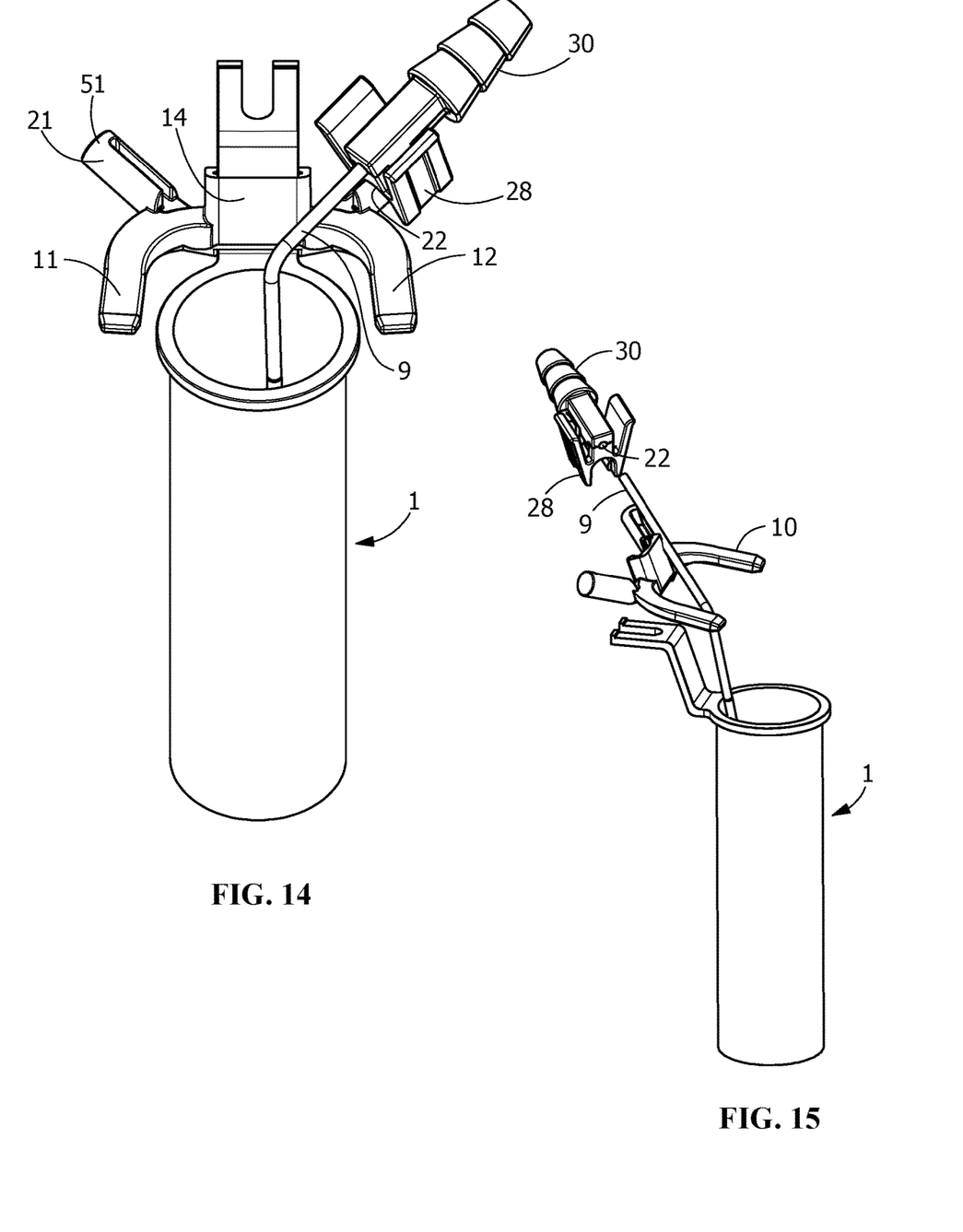
FIG. 14 is a front perspective view of a third exemplary tubular retractor securement frame attached to a tubular retractor and a surgical device, according to an embodiment of the present disclosure.
FIG. 15 is an exploded side perspective view of the tubular retractor securement frame, tubular retractor, and surgical device of FIG. 14, according to an embodiment of the present disclosure.

Referring to FIGS. 14 and 15, the first device emplacement 21 may include a projection 51 arranged to be gripped by a clip 28 of a leur adapter 30 into which the surgical tool 9 is inserted. In one embodiment, the surgical tool 9 is free of direct contact with the tubular retractor securement frame 10.

Figures 16, 17:
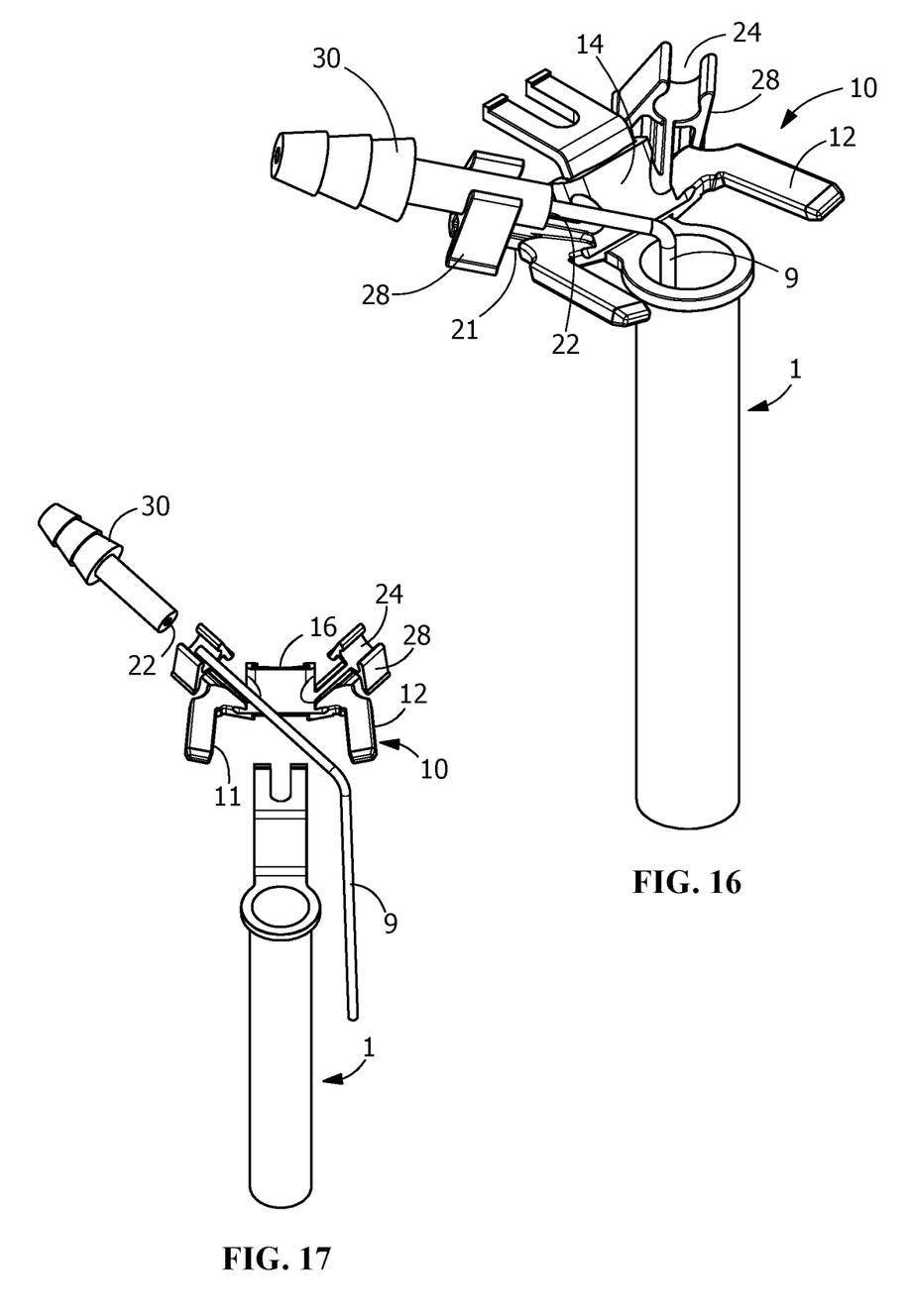
FIG. 16 is a front-side perspective view of a fourth exemplary tubular retractor securement frame attached to a tubular retractor and a surgical device, according to an embodiment of the present disclosure.
FIG. 17 is an exploded side perspective view of the tubular retractor securement frame, tubular retractor, and surgical device of FIG. 16, according to an embodiment of the present disclosure.
Figure 18:
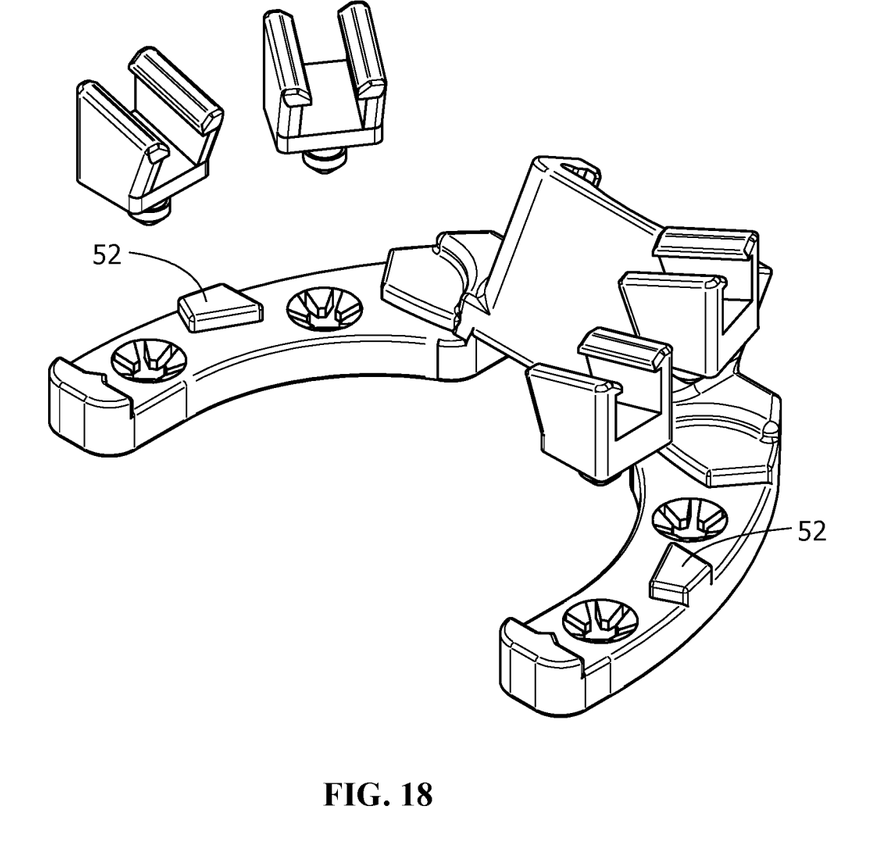
FIG. 18 is an exploded front-side perspective view of a fifth exemplary tubular retractor securement frame, according to an embodiment of the present disclosure.
Figure 19:
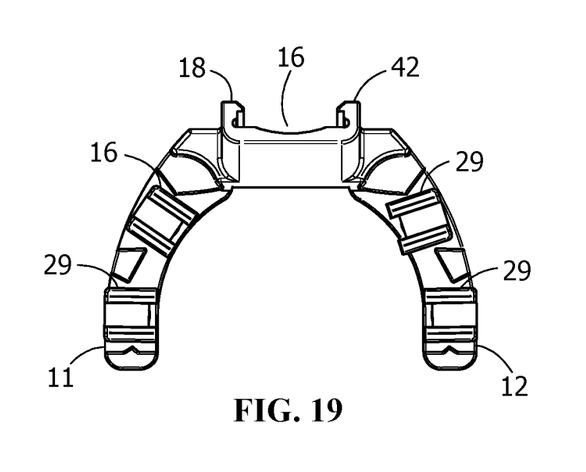
FIG. 19 is a top view of the tubular retractor securement frame of FIG. 18, according to an embodiment of the present disclosure.
Figure 20:
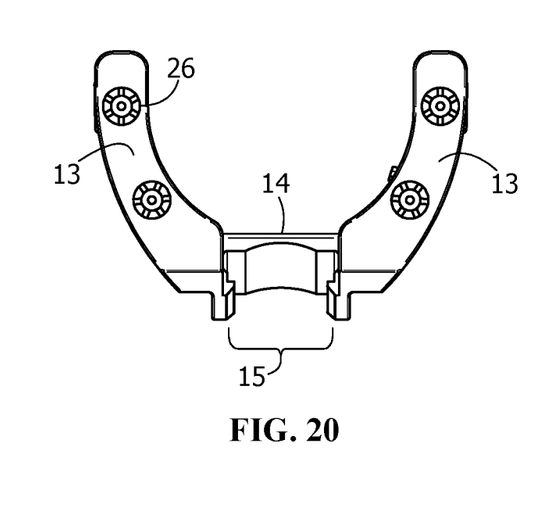
FIG. 20 is a bottom view of the tubular retractor securement frame of FIG. 18, according to an embodiment of the present disclosure.
Figure 21:
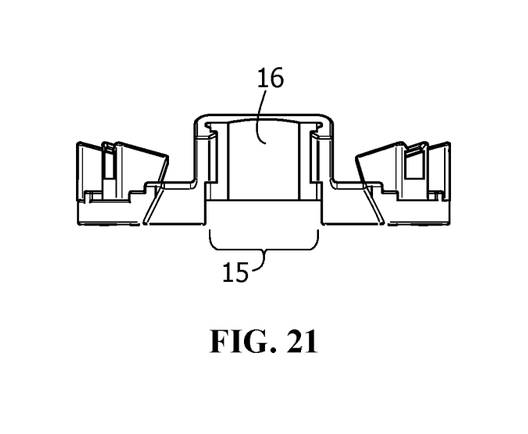
FIG. 21 is a rear view of the tubular retractor securement frame of FIG. 18, according to an embodiment of the present disclosure.
Figure 22:
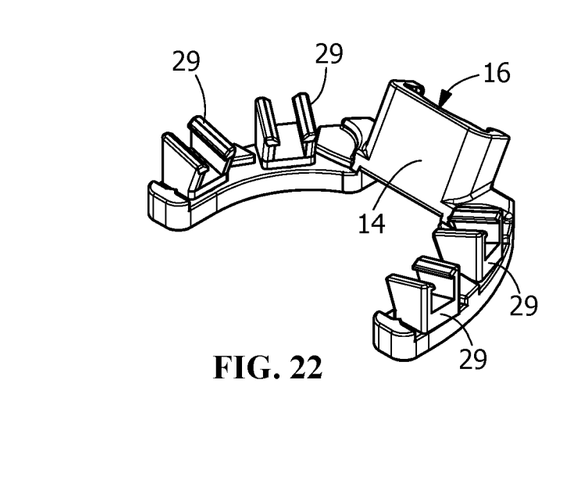
FIG. 22 is a top-front-side perspective view of the tubular retractor securement frame of FIG. 18, according to an embodiment of the present disclosure.
Figure 23:
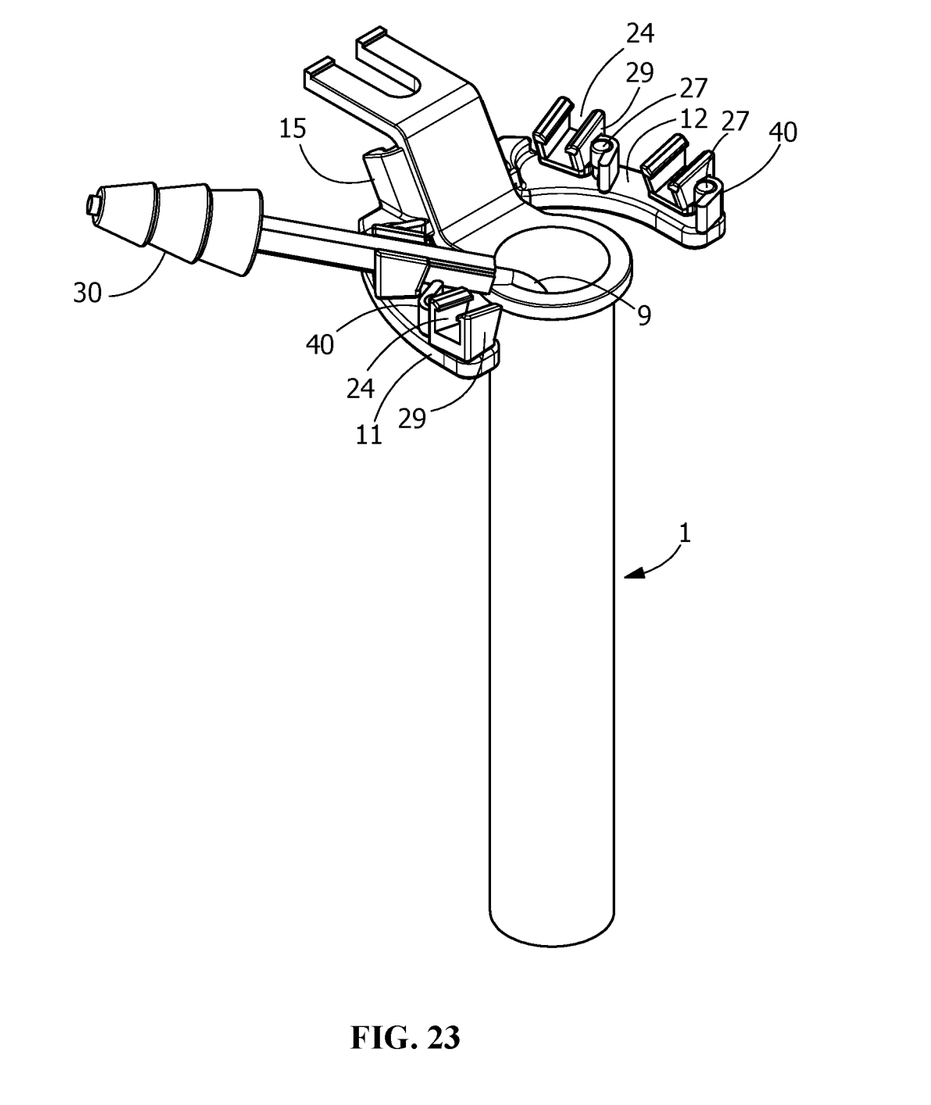
FIG. 23 is a front-side perspective view of a sixth exemplary tubular retractor securement frame attached to a tubular retractor and a surgical device, according to an embodiment of the present disclosure.
Figure 24:
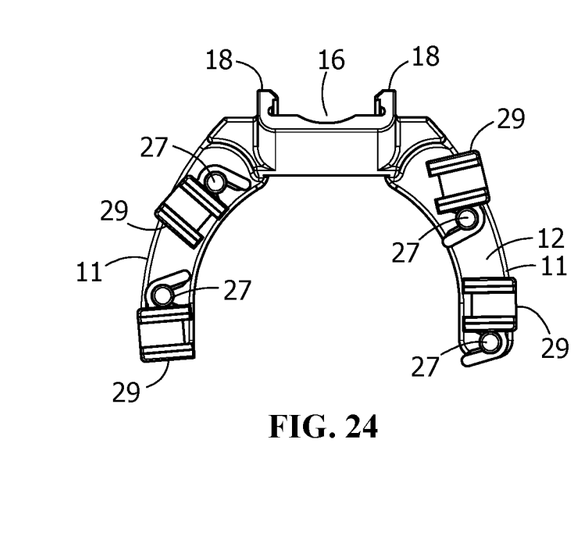
FIG. 24 is a top view of the tubular retractor securement frame of FIG. 23, according to an embodiment of the present disclosure.
Figure 25:
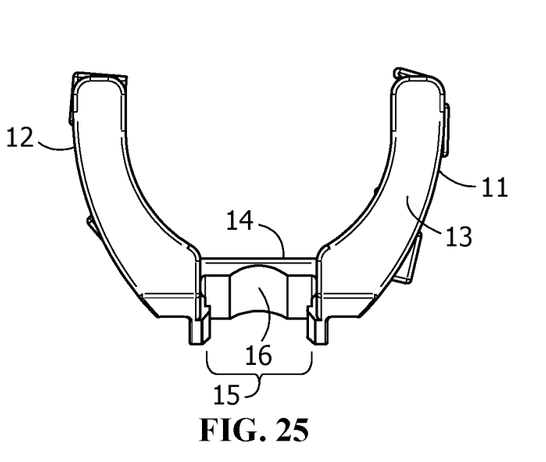
FIG. 25 is a bottom view of the tubular retractor securement frame of FIG. 23, according to an embodiment of the present disclosure.
Figure 26:
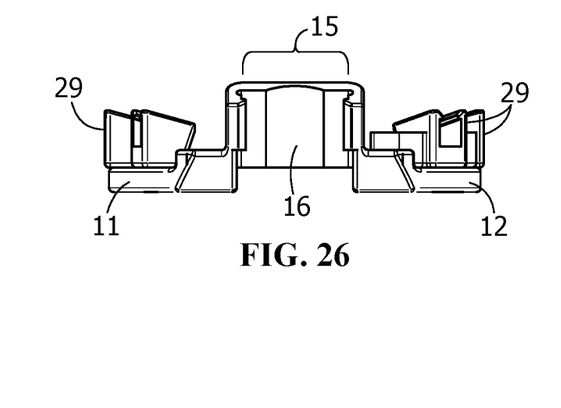
FIG. 26 is a rear view of the tubular retractor securement frame of FIG. 23, according to an embodiment of the present disclosure.
Figure 27:
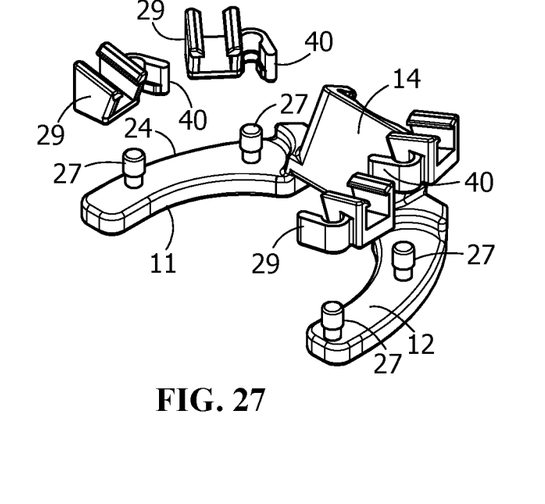
FIG. 27 is a top-front-side exploded perspective view of the tubular retractor securement frame of FIG. 23, according to an embodiment of the present disclosure.
Figure 28:
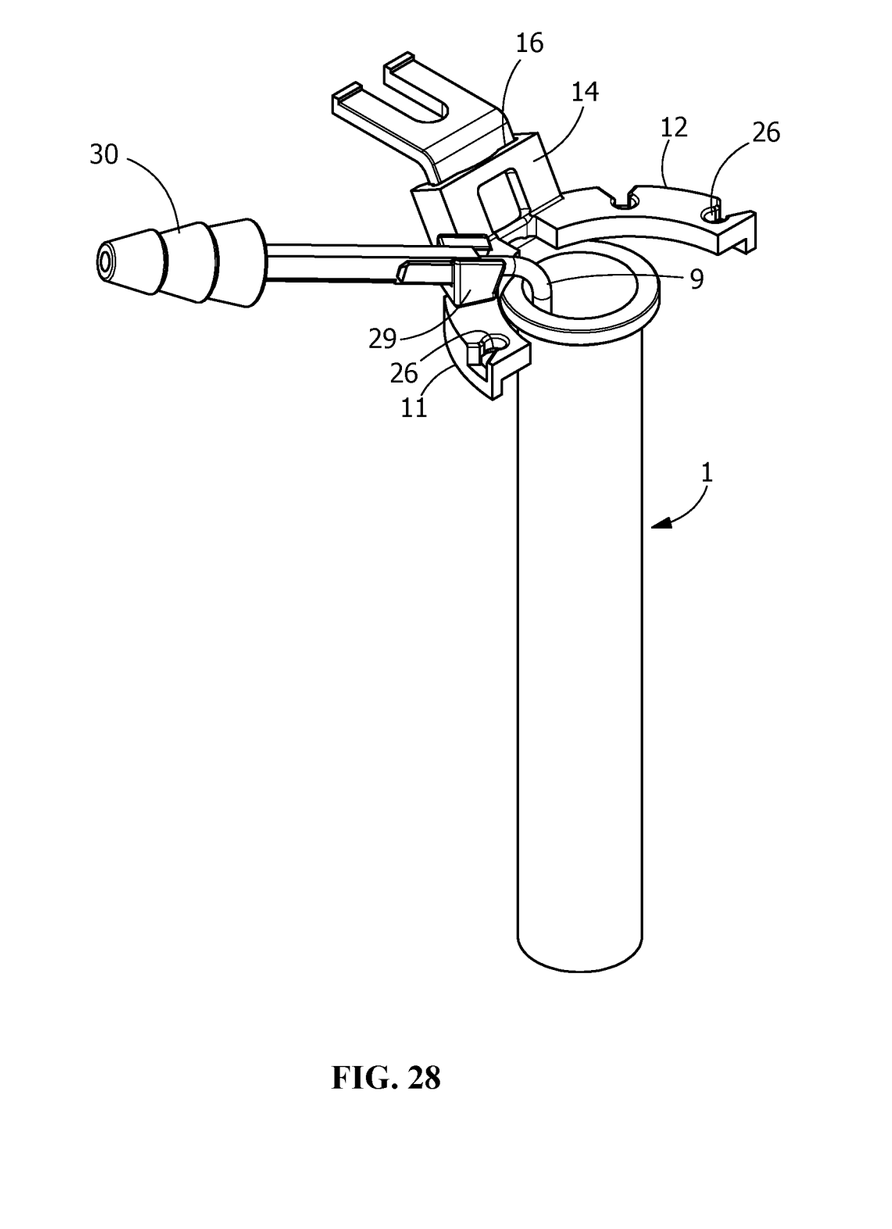
FIG. 28 is a front-side perspective view of a seventh exemplary tubular retractor securement frame attached to a tubular retractor and a surgical device, according to an embodiment of the present disclosure.
Figure 29:
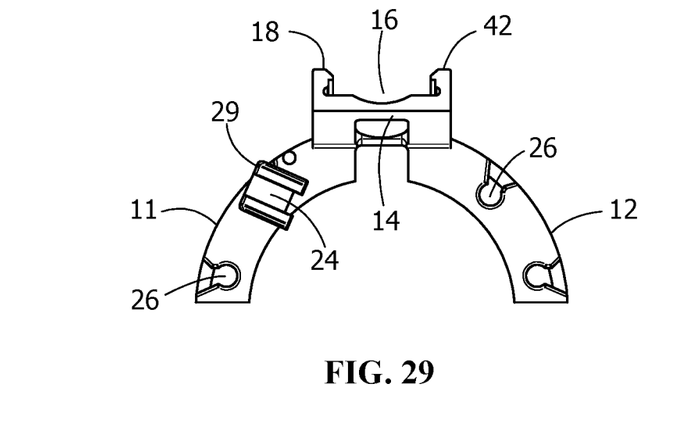
FIG. 29 is a top view of the tubular retractor securement frame of FIG. 28, according to an embodiment of the present disclosure.
Figure 30:
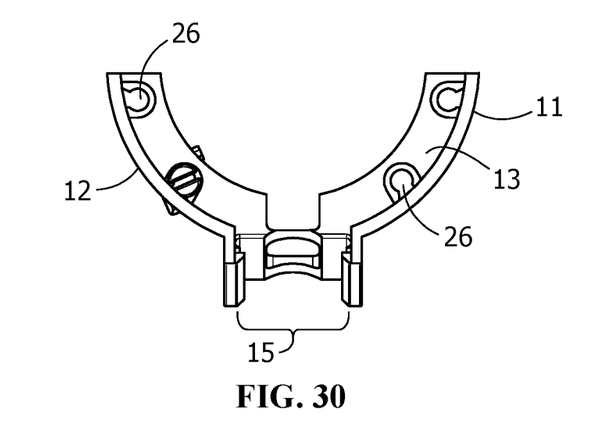
FIG. 30 is a bottom view of the tubular retractor securement frame of FIG. 28, according to an embodiment of the present disclosure.
Figure 31:
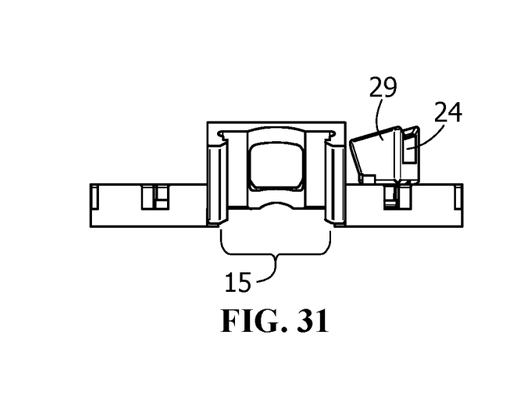
FIG. 31 is a rear view of the tubular retractor securement frame of FIG. 28, according to an embodiment of the present disclosure.
Figure 32:
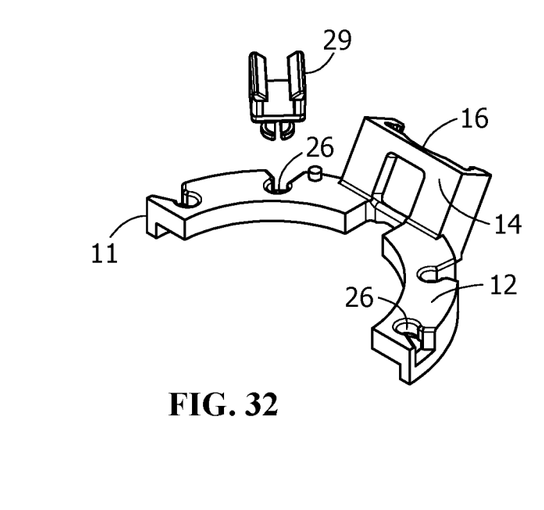
FIG. 32 is a top-front-side exploded perspective view of the tubular retractor securement frame of FIG. 28, according to an embodiment of the present disclosure.

Referring to FIGS. 16 and 17, the first device emplacement 21 may include a channel 24 arranged to grip a leur adapter 30 into which the surgical tool 9 is inserted. In one embodiment, the surgical tool 9 is free of direct contact with the tubular retractor securement frame 10.

Referring to FIGS. 18-22 and 28-32, the first device emplacement 21 may include a rotatable channel member 29 inserted in a receptacle 26 disposed in one of the first flexor arm 11 or the second flexor arm 12. The receptacle 26 may be closed at a bottom surface 13 of the first flexor arm 11 or the second flexor arm 12 or pass entirely through the first flexor arm 11 or the second flexor arm 12. The rotatable channel member 29 may be reversibly or irreversibly inserted in the receptacle 26. The first flexor arm 11 and the second flexor arm 12 may independently include any suitable number of such rotatable channel members 29 disposed in such receptacles 26. The rotatable channel member 29 may be inserted in the receptacle 26 either about in a plane defined by the first flexor arm 11 and the second flexor arm 12 (FIGS. 28-32) or about orthogonal to the plane defined by the first flexor arm 11 and the second flexor arm 12 (FIGS. 18-22). As used herein, "about in a plane" indicates being with 15° of the plane. The first flexor arm 11 or the second flexor arm 12 may include any suitable number of restrictors 52 limiting the rotational freedom of the rotatable channel member 29.

Referring to FIGS. 23-27, the first device emplacement 21 may include a rotatable channel member 29 reversibly mounted on a projection 27 extending from one of the first flexor arm 11 or the second flexor arm 12. The rotatable channel member 29 may be reversibly or irreversibly mounted on the projection 27. The rotatable channel member 29 may include a securement arm 40 extending from the rotatable channel member 29 which mounts the rotatable channel member 29 on the projection 27. The first flexor arm 11 and the second flexor arm 12 may independently include any suitable number of such rotatable channel members 29 disposed on such projections 27. The first flexor arm 11 or the second flexor arm 12 may include any suitable number of restrictors 52 limiting the rotational freedom of the rotatable channel member 29.

Referring to FIGS. 1-32, the mounting bracket 45 may be a cantilever snap-fit connector 15 with the first rail 18 being a first cantilever 48, the second rail 42 being a second cantilever 49, and the first pair of receptacles 17 being defined by a first hook 20 of the first cantilever 48 and a second hook 43 of the second cantilever 49, such that the mounting bracket 45 is mountable to the retractor arm 5 by applying a normal force to the mounting bracket 45 while the mounting bracket 45 is aligned with and in contact with the retractor handle 12. The second pair of receptacles 16 may further be defined by a third hook 19 of the first cantilever 48 and a fourth hook 44 of the second cantilever 49. Each of the first hook 20, the second hook 43, the third hook 19, and the fourth hook 44 may include a bullnose conformation suitable for snap-fit activation.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced. And, more specifically with respect to the directional movement of an implant according to the methods of the disclosure, sideways refers to the general direction of movement within the disc space between the endplates from the position of the inserted instruments toward one or the other of the contralateral and ipsilateral portions of the disc space. In the case of a TLIF procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and also in a rotational or pivotal motion. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

What is claimed is:

1. A tubular retractor securement frame, comprising:
   a mounting bracket, including:
      an elastically deformable plate;
      a first rail extending about orthogonal from the elastically deformable plate;
      a second rail extending about orthogonal from the elastically deformable plate such that the second rail is about parallel to the first rail; and
      a first pair of receptacles disposed facing one another, one each, in the first rail and the second rail, the first pair of receptacles being arranged to receive a retractor arm extending from a tubular retractor at a first fixed angle;
   a first flexor arm extending from the mounting bracket adjacent to the first rail;
   a second flexor arm extending from the mounting bracket adjacent to the second rail; and
   a first device emplacement oriented to receive and hold in-place a surgical tool disposed at least partially within the tubular retractor at a fixed position and orientation relative to the tubular retractor when the mounting bracket is mounted to the retractor arm,
   wherein the first flexor arm and the second flexor arm are positioned such that applying pressure to flex the first flexor arm and the second flexor arm toward one another expands a distance between the first rail and the second rail sufficient to accept the retractor arm into the first pair of receptacles and for the retractor arm to be removed from the first pair of receptacles, and upon releasing the pressure the distance between the first rail and the second rail reverts so as to inhibit the retractor arm from being inserted or removed from the first pair of receptacles, and
   wherein the first flexor arm and the second flexor arm are positioned so as not to occlude visualization through the tubular retractor when the mounting bracket is mounted onto the retractor arm.

2. The tubular retractor securement frame of claim 1, further including a second pair of receptacles disposed facing one another, one each, in the first rail and the second rail, the second pair of receptacles being arranged to receive the retractor arm extending from the tubular retractor at a second fixed angle distinct from the first fixed angle.

3. The tubular retractor securement frame of claim 2, wherein the first fixed angle is between 1080 and 112°, and the second fixed angle is between 1180 and 122°.

4. The tubular retractor securement frame of claim 1, further including a second device emplacement oriented to receive and hold in-place an additional surgical tool disposed at least partially within the tubular retractor at an additional fixed position and orientation relative to the tubular retractor when the mounting bracket is mounted to the retractor arm.

5. The tubular retractor securement frame of claim 1, wherein the surgical tool includes a fluid transport assembly providing at least one of suction or irrigation into the tubular retractor.

6. The tubular retractor securement frame of claim 5, wherein the first device emplacement includes a leur adapter in fluid communication with the surgical tool and a remote suction or irrigation source.

7. The tubular retractor securement frame of claim 1, wherein the surgical tool includes a lighting element providing illumination into the tubular retractor.

8. The tubular retractor securement frame of claim 1, wherein the first rail and the second rail extend from the elastically deformable plate away from the tubular retractor when the mounting bracket is mounted on the retractor arm.

9. The tubular retractor securement frame of claim 1, wherein the first rail and the second rail extend from the elastically deformable plate toward the tubular retractor when the mounting bracket is mounted on the retractor arm.

10. The tubular retractor securement frame of claim 1, further including a crossbar slidably mounted on at least one of the first flexor arm or the second flexor arm, the crossbar reversibly attaching to the mounting bracket so as to secure the surgical tool against an inner wall of the tubular retractor.

11. The tubular retractor securement frame of claim 1, further including a plurality of grooves disposed along each of the first flexor arm and the second flexor arm, the plurality of grooves being disposed about parallel to an axis of the tubular retractor and facing the tubular retractor.

12. The tubular retractor securement frame of claim 1, wherein the first device emplacement includes an elongate channel extending for greater than a thickness of either the first flexor arm or the second flexor arm over which the first device emplacement extends.

13. The tubular retractor securement frame of claim 1, wherein the first device emplacement includes a channel arranged to grip a leur adapter into which the surgical tool is inserted, the surgical tool being free of direct contact with the tubular retractor securement frame.

14. The tubular retractor securement frame of claim 1, wherein the first device emplacement includes a projection arranged to be gripped by a channel of a leur adapter into which the surgical tool is inserted, the surgical tool being free of direct contact with the tubular retractor securement frame.

15. The tubular retractor securement frame of claim 1, wherein the first device emplacement includes a rotatable channel member reversibly inserted in a receptacle disposed in one of the first flexor arm or the second flexor arm.

16. The tubular retractor securement frame of claim 15, wherein the first flexor arm or the second flexor arm includes a restrictor limiting the rotational freedom of the rotatable channel member.

17. The tubular retractor securement frame of claim 15, wherein the first flexor arm and the second flexor arm together include a plurality of receptacles for receiving the rotatable channel member.

18. The tubular retractor securement frame of claim 15, wherein the rotatable channel member reversibly inserts into the receptacle in a plane defined by the first flexor arm and the second flexor arm.

19. The tubular retractor securement frame of claim 15, wherein the rotatable channel member reversibly inserts into the receptacle orthogonal to a plane defined by the first flexor arm and the second flexor arm.

20. The tubular retractor securement frame of claim 1, wherein the first device emplacement includes a rotatable channel member reversibly mounted on a projection extending from one of the first flexor arm or the second flexor arm.

21. The tubular retractor securement frame of claim 1, wherein the mounting bracket is a cantilever snap-fit connector with the first rail being a first cantilever, the second rail being a second cantilever, and the first pair of receptacles being defined by a first hook of the first cantilever and a second hook of the second cantilever, such that the mounting bracket is mountable to the retractor arm by applying a normal force to the mounting bracket while the mounting bracket is aligned with and in contact with a retractor handle.

\* \* \* \* \*